(12) United States Patent
Daly

(10) Patent No.: US 11,504,507 B2
(45) Date of Patent: Nov. 22, 2022

(54) METHOD OF MANUFACTURING A SILICONE MEDICAL BALLOON

(71) Applicant: Cook Medical Technologies LLC, Bloomington, IN (US)

(72) Inventor: Mark D. Daly, Ellettsville, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 214 days.

(21) Appl. No.: 17/026,529

(22) Filed: Sep. 21, 2020

(65) Prior Publication Data

US 2021/0093842 A1   Apr. 1, 2021

Related U.S. Application Data

(60) Provisional application No. 62/907,203, filed on Sep. 27, 2019.

(51) Int. Cl.
| | |
|---|---|
| *A61M 25/10* | (2013.01) |
| *B29C 48/10* | (2019.01) |
| *B29C 48/00* | (2019.01) |
| *B29C 35/08* | (2006.01) |
| *B29C 48/255* | (2019.01) |
| *B29L 31/00* | (2006.01) |
| *B29K 83/00* | (2006.01) |

(52) U.S. Cl.
CPC ...... *A61M 25/1029* (2013.01); *B29C 35/0805* (2013.01); *B29C 48/0017* (2019.02); *B29C 48/022* (2019.02); *B29C 48/10* (2019.02); *B29C 48/255* (2019.02); *A61M 2207/10* (2013.01); *B29C 2035/0827* (2013.01); *B29K 2083/00* (2013.01); *B29K 2833/12* (2013.01); *B29K 2909/08* (2013.01); *B29L 2031/7543* (2013.01)

(58) Field of Classification Search
None
See application file for complete search history.

(56) References Cited

U.S. PATENT DOCUMENTS 5,762,996 A * 6/1998 Lucas ............... A61L 29/06
427/2.3
6,875,197 B1 * 4/2005 Simhambhatla .. A61M 25/1029
604/103.08

* cited by examiner

*Primary Examiner* — Robert J Grun
(74) *Attorney, Agent, or Firm* — Crowell & Moring LLP

(57) ABSTRACT

A method of forming a balloon for a medical device is provided including extruding a cylindrical tube of silicone material, partially curing the cylindrical tube, inflating the cylindrical tube, and fully curing the balloon. The cylindrical tube is partially cured by exposing the cylindrical tube to a first ultraviolet light source. The cylindrical tube is inflated within a mold to form the balloon. The balloon is fully cured by exposing the balloon to a second ultraviolet light source.

14 Claims, 5 Drawing Sheets

METHOD OF MANUFACTURING A SILICONE MEDICAL BALLOON

CROSS-REFERENCE TO RELATED APPLICATIONS

This application claims priority U.S. Provisional Application Ser. No. 62/907,203, filed Sep. 27, 2019, which is incorporated herein by reference in its entirety.

TECHNICAL FIELD

This disclosure relates to methods of manufacturing silicone products and in particularly to methods of manufacturing silicone medical balloons.

BACKGROUND

The statements in this section merely provide background information related to the present disclosure and may not constitute prior art.

Medical Balloons for use with catheters are typically manufactured from silicone or a polymer material. The balloons are typically formed in a mold and then cured or heat set by heating the material of the balloon for an extended period of time. However, this process is slow, requiring between 20-60 minutes to cure a single balloon. Furthermore, prolonged heating of the balloon material can cause imperfections in the balloon which could cause the balloon to fail when in use, endangering patients. Therefore, it is desirable to have an efficient method of forming medical balloons in a low temperature environment.

SUMMARY

Further areas of applicability will become apparent from the description provided herein. It should be understood that the description and specific examples are intended for purposes of illustration only and are not intended to limit the scope of the present disclosure.

In one embodiment, a method of forming a balloon for a medical device is provided including extruding a cylindrical tube of silicone material, partially curing the cylindrical tube, inflating the cylindrical tube, and fully curing the balloon. The cylindrical tube is partially cured by exposing the cylindrical tube to a first ultraviolet light source. The cylindrical tube is inflated within a mold to form the balloon. The balloon is fully cured by exposing the balloon to a second ultraviolet light source.

In another embodiment, a method of forming a balloon for a medical device is provided, including extruding liquid silicone rubber to form a hollow element, partially curing the hollow element to form a semi-solid tube, inflating the semi-solid tube of the hollow element, and fully curing the hollow element to form a balloon. The hollow element may be partially cured by exposing the liquid silicone rubber to a first ultraviolet light source. The semi-solid hollow element may be cured within a mold. The hollow element may be fully cured by exposing the semi-solid hollow element to a second ultraviolet light source.

In yet another embodiment, an apparatus for manufacturing a balloon for use in a medical device may be provided, including an extruder, a first ultraviolet light source, a liquid source, a mold, and a second ultraviolet light source. The extruder is arranged to extrude liquid silicone rubber into a cylindrical tube. The first ultraviolet light source is arranged to partially cure the cylindrical tube. The liquid source may be used to inflate the partially cured cylindrical tube into a balloon. The mold may contain the inflation of the partially cured balloon. The second ultraviolet light source may be used to fully cure the balloon.

BRIEF DESCRIPTION OF THE DRAWINGS

The embodiments may be better understood with reference to the following drawings and description. The components in the figures are not necessarily to scale. Moreover, in the figures, like-referenced numerals designate corresponding parts throughout the different views.

The drawings described herein are for illustration purposes only and are not intended to limit the scope of the present disclosure in any way.

DETAILED DESCRIPTION

The following description is merely exemplary in nature and is not intended to limit the present disclosure, application, or uses.

In one example, a method of forming a balloon for a medical device is disclosed including extruding a cylindrical tube of silicone material, partially curing the cylindrical tube, inflating the cylindrical tube, and fully curing the balloon. The cylindrical tube is partially cured by exposing the cylindrical tube to a first ultraviolet light source. The cylindrical tube is inflated within a mold to form the balloon. The balloon is fully cured by exposing the balloon to a second ultraviolet light source.

One technical advantage of the systems and methods described below may be that the extrusion system may be used to manufacture balloons for use in medical devices at a much faster rate than existing methods. Existing methods involve extruding material into a mold and heat-curing the material, which is a lengthy process. Faster manufacturing may allow the cost of production of the balloons to be reduced.

Another technical advantage of the systems and methods described below may be that the extrusion system may be used to may be used to prevent formation of material defects present using existing methods of manufacturing. Molding material into the shape of a balloon, may cause seams to form where material meets about the circumference of the balloon. These seams may be weak points on the balloon which may cause the balloon to rupture when under stress. Furthermore, prolonged heating to cure the material of the balloon may cause brittleness or other material defects to form in the balloon, increasing the chances that the balloon may rupture when under stress. Rupture of the balloon may cause serious harm to a patient if the balloon ruptures while inside a body cavity of a patient.

Figure 1:
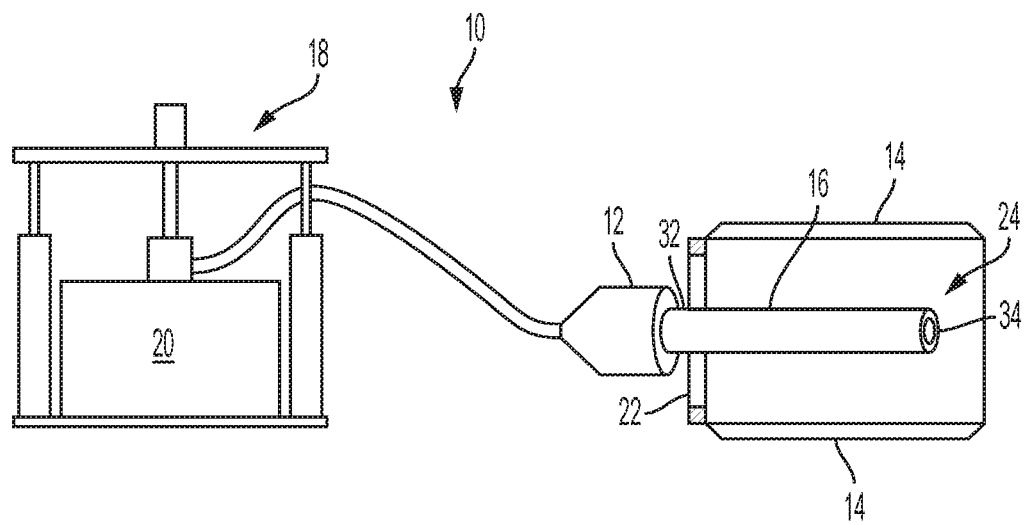
FIG. 1 illustrates a partial cross-sectional side view of a first example of an extrusion system including an extruder, a pump, a curing chamber, and silicone material.

FIG. 1 illustrates a partial cross-sectional side view of an extruder system 10. The extruder system 10 may be any system which processes raw material and extrudes the material into a linear shape. Examples of the extruder system 10 may include a pumping system, various crossheads, an UV curing system and a take up or cut to length system. The extruder system 10 may extrude material, such as liquid silicone rubber, another silicone elastomer, or a polymer to form a hollow element 16. The hollow element 16 may be any structure which is extruded from the extruder 10 system, which defines an internal a cavity or lumen, and which may be formed into a balloon. Examples of the hollow element 16 may include a cylindrical tube, a bubble, or a partially spherical object. The hollow element 16 may include a lumen (38 in FIG. 2) extending from a first end 32 to a second end 34 of the hollow element 16.

The extruder system 10 may include a pump 18, an extruder 12 and a supply 20 of material to be extruded. The pump 18 may be any device which transfers material from the supply 20 to the extruder 12. Examples of the pump 18 may include an air pump, or an inert fluid displacement pump. The supply 20 of material may be any container which may hold the material and allow it to be pumped to the extruder 12. The extruder 12 may be any device which extrudes material into a specific shape or configuration. Examples of the extruder 12 may include a spiral mandrel extruder, a ram type extruder, or a screw type extruder.

The hollow element 16 may be extruded into a curing chamber 24. The curing chamber 24 may be any apparatus in which material such as liquid silicone rubber may be cured or partially cured. Examples of the curing chamber 24 may include a cavity, a container, or an open curing environment. The curing chamber 24 may include an ultraviolet light source 14. The ultraviolet light source 14 may be any device which emits ultraviolet radiation which has a frequency and intensity to cure or partially cure material such as liquid silicone rubber. Examples of the ultraviolet light source 14 may include an array of light emitting diodes, a microwave gas discharge lamp, or an electrode gas discharge lamp.

As illustrated in FIG. 1, the curing chamber 24 may be a first curing chamber 24 having a first ultraviolet light source 14. The ultraviolet light source 14 within the curing chamber 24 may be arranged to partially cure or fully cure the material within the curing chamber 24. As illustrated in FIG. 1, the first ultraviolet light source 14 within the first curing chamber 24 may be arranged to only partially cure the material within the first curing chamber 24. In the embodiment of the material being liquid silicone rubber, partially curing the material may involve converting the material from a liquid state to a semi-solid state. The material may be partially cured to an extent where the material is still malleable but is able to maintain a shape for at least a short period of time.

The extruder system 10 may also include a cutting apparatus 22. The cutting apparatus 22 may be any device which may be used to separate the hollow element 16 from the extruder 12. Examples of the cutting apparatus 22 may include a single blade, crossing blades, or an amplified electromagnetic radiation cutting system. The cutting apparatus 22 may be integrated into the curing chamber 24, may be integrated into the extruder 12, or may be entire separate from the both the curing chamber 24 or the extruder 12.

Figure 2:
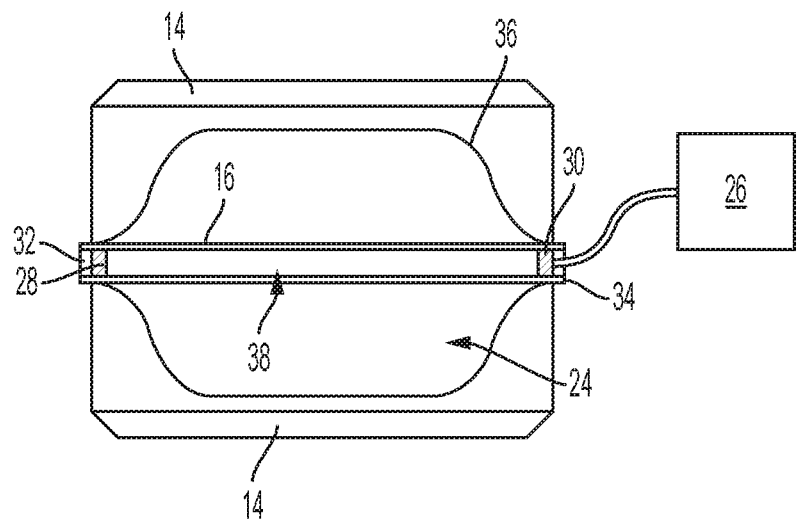
FIG. 2 illustrates a cross-sectional side view of a second example of the curing chamber including silicone material.

FIG. 2 illustrates an example of a second curing chamber 24 including a second ultraviolet light source 14 and a mold 36. In some embodiments, the hollow element 16 may be placed within a mold 36 after being partially cured. Once placed in the mold 36, the first end 32 of the hollow element 16 may be sealed by a first seal 28, and the second end 34 of the hollow element 16 may be sealed by a second seal 30. The first seal 28 and second seal 30 may be placed within the lumen 38 of the hollow element 16 in some embodiments, or may be placed against the exterior of the hollow element 16. Once the lumen 38 of the hollow element 16 has been sealed, the hollow element 16 may be inflated with a fluid pumped into the lumen 38 by a fluid source 26. The fluid source 26 may be any device which delivers fluid to the lumen 38 of the hollow element 16. An example of the fluid source may be a pump. The fluid delivered to inflate the hollow element may be any fluid which does not interfere with the curing process, such as air, water, or saline.

Inflation of the hollow element 16 may cause the partially cured hollow element 16 to take on the shape of the interior of the mold 36. The mold 36 may have an interior shaped like the desired shape of the medical balloon. The semi-solid state of the partially cured hollow element 16 may allow the hollow element 16 to be more responsive in inflating while preventing rupture of the hollow element 16.

Once the hollow element has been inflated to the conform to the shape of the interior of the mold 36, the material of the hollow element 16 may be fully cured by illuminating the hollow element with the second ultraviolet light source 14. To facilitate this illumination, some embodiments of the mold 36 may be transparent, or at least transparent to ultraviolet radiation, to allow light from the second ultraviolet light source to pass through the mold 36 to cure the hollow element 16. For example, the mold 36 may be made of quartz glass or polymethyl methacrylate (PMMA). Once the hollow element 16 has been fully cured into a solid balloon, the hollow element 16 may be deflated, the first seal 28 and the second seal 30 may be removed, and the hollow element 16 may be removed from the mold 36 and the second curing chamber 24.

The first ultraviolet light source 14 and the second ultraviolet light source 14 may have different properties to partially cure or fully cure the material. For example, the first ultraviolet light source 14 may have a wavelength which is greater than the second ultraviolet light source 14. The first ultraviolet light source 14 may emit radiation with a wavelength between 320 nm-520 nm. The second ultraviolet light source 14 may emit radiation with a wavelength between 200 nm-400 nm.

Alternatively, the material of the hollow element 16 may be exposed to the first ultraviolet light source 14 for less time than the material of the hollow element 16 is exposed to the second ultraviolet light source 14. For example the material of the hollow element 16 may be exposed to the first ultraviolet light source 14 for between 0.5 sec-60 sec to partially cure the material. Comparatively, the material of the hollow element 16 may be exposed to the second ultraviolet light source 14 for between 5 sec-300 sec to fully cure the material. Difference in time to partially cure or fully cure the material are dependent upon the width of the material and the composition of the material.

Alternatively, the partial curing or full curing of the material of the hollow element 16 may occur with the first ultraviolet light source 14 having an intensity which is less than an intensity of the second ultraviolet light source 14.

The intensity of both of the ultraviolet light sources 14 may vary between 4000 W/cm² to 5000 W/cm². For example the intensity of the first ultraviolet light source 14 may be 4000 W/cm² and the intensity of the second ultraviolet light source 14 may be 5000 W/cm².

The temperature within the curing chamber 24 may vary depending upon the conditions of the ultraviolet light sources 14. However, the temperature within the curing chamber 24 may be significantly lower than temperatures used when heat curing material. For example, the temperature within the curing chamber may be between 25° C. and 40° C.

Figure 3:
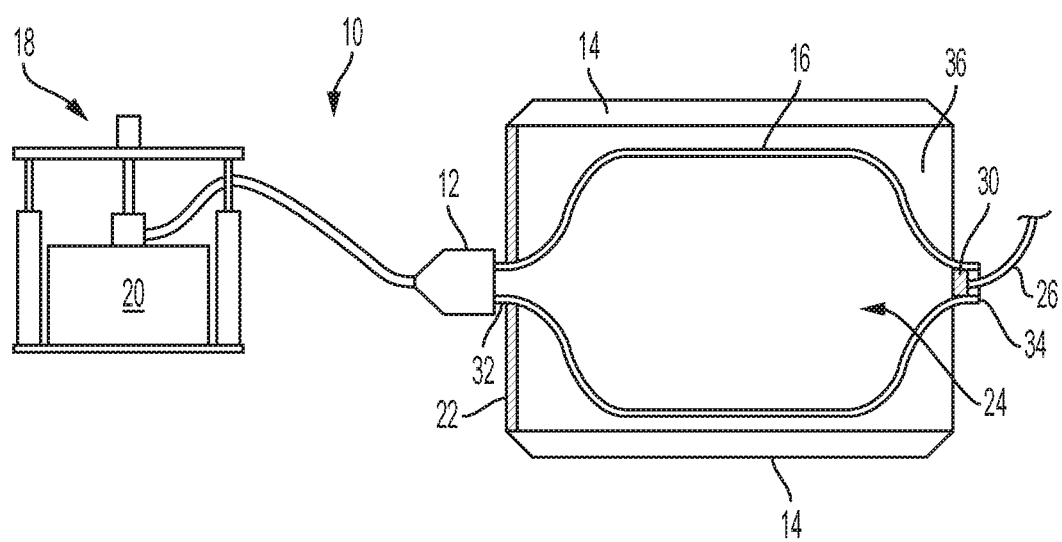
FIG. 3 illustrates a partial cross-sectional side view of a second example of the extrusion system including the extruder, the pump, the curing chamber, and silicone material.

FIG. 3 illustrates a partial cross-sectional side view of the extruder system 10 and the curing chamber 24. In some embodiments, only a single curing chamber 24 and a single ultraviolet light source 14 may be needed to partially cure, inflate, and fully cure the hollow element 16. In such an embodiment, the extruder 10 may be coupled to a first end of the mold 36 to extrude the material of the hollow element 16 directly into the mold 36. The material of the hollow element 16 may then be partially cured by the ultraviolet light source 14 used on a first setting or in a first condition. Additionally, the fluid source 26 may be coupled to a second end of the mold 36 to seal the lumen 38 of the hollow element 16 and inflate the hollow element 16. The material of the hollow element 16 may then be fully cured by the ultraviolet light source 14 used on a second setting or in a second condition.

Figure 4:
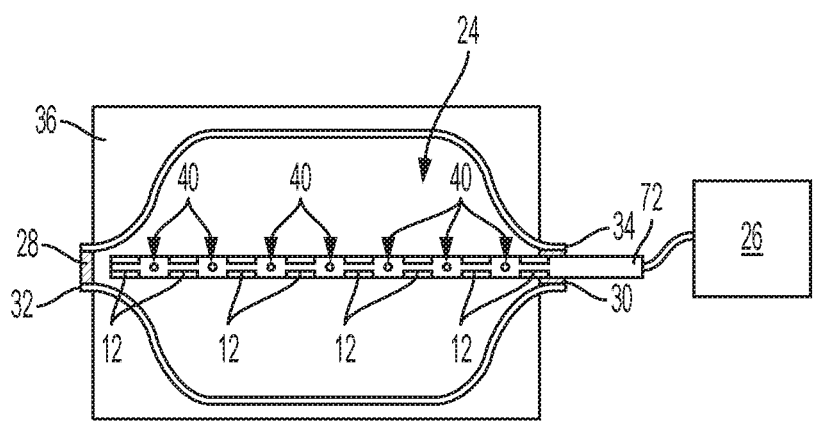
FIG. 4 illustrates a cross-sectional side view of a fourth example of the curing chamber including the silicone material and an internal curing device.

FIG. 4 illustrates a partial cross-sectional view of another embodiment of the curing chamber 24. In some embodiments, the mold 36 may not be transparent to ultraviolet radiation. In such an embodiment, it may be desirable to cure the material of the hollow element 16 from within the lumen 38 of the hollow element 16 utilizing an internal curing device 72. The internal curing device 72 may be any device configured to be placed within the lumen 38 of the hollow element 16 to partially or fully cure the material of the hollow element 16. For example, the internal curing device 72 may extend along most or all of the length of the hollow element 16 and may include a series of ultraviolet light sources 14 arranged on the outer surface of the internal curing device 72. Once the hollow element 16 has been secured within the mold 36, the internal curing device 72 may be inserted into the lumen 38 of the hollow element 16 to partially cure the material of the hollow element 16.

In some embodiments, the first seal 28 and the second seal 30 may seal the lumen 38 of the hollow element while the internal curing device 72 is arranged within the lumen 38. The hollow element 16 may then be inflated with fluid from the fluid source, extending through one of the first seal 28 or the second seal 30, or passing through ports 40 arranged on the internal curing device 72. Once inflated, the ultraviolet light source 14 of the internal curing device 72 may fully cure the material of the hollow element 16.

Figure 5:
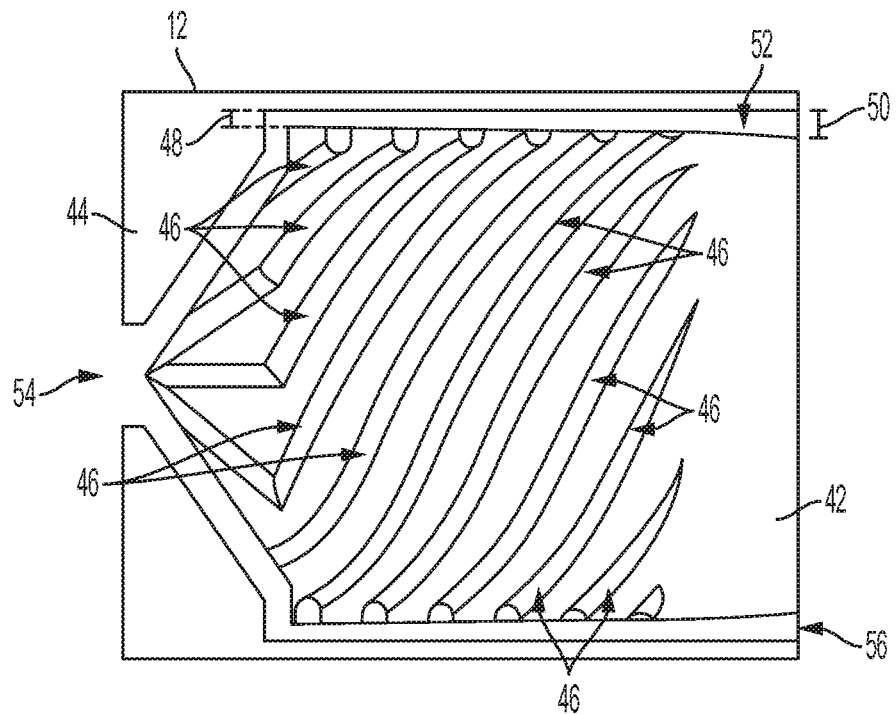
FIG. 5 illustrates a cross-sectional side view of a third example of the extruder including a casing and a mandrel.

FIG. 5 illustrates a cross-sectional side view of an example of the extruder 12 including a casing 44 and a mandrel 42. The casing 44 may be any component which define the interior of the extruder 12. The shape of the inner surface of the casing 44 may define the characteristics and shape of the outer surface of the hollow element. The casing 44 may have an inlet 54 on a first end to allow material to enter the extruder 12. The casing 44 may also have an outlet 56 at a second end to allow the extruded material to exit from the extruder 12.

The mandrel 42 may be any part of the extruder 12 which fits into the interior of the casing 44 and guides material passing through the extruder 12 from the inlet 54 to the outlet 56. The mandrel 42 may be smooth or may have grooves directing the flow of material from the inlet 54 to the outlet 56. For example, as illustrated in FIG. 5, the mandrel 42 may include a series of spiral grooves 46 spaced about the circumference of the outer surface of the mandrel 42. The spiral grooves 46 may inject material into the hollow element 16 at different lengths as it is being extruded. The depth of the spiral grooves 46 may decrease as the mandrel 42 extends from the inlet 54 to the outlet 56. The spiral grooves 46 may terminate before reaching the outlet 56 of the extruder 12.

A gap 52 may exist between the casing 44 and the mandrel 42 defining a wall (58 in FIG. 6) of the hollow element 16. The gap 52 may have a first width 48 proximate to the inlet 54 of the extruder 12 and may have a second width 50 at the outlet 56 of the extruder 12. The increasing width of the gap 52 may be attributed to the material which is added from the spiral grooves 46 as the material is extruded from the inlet 54 to the outlet 56.

Figure 6:
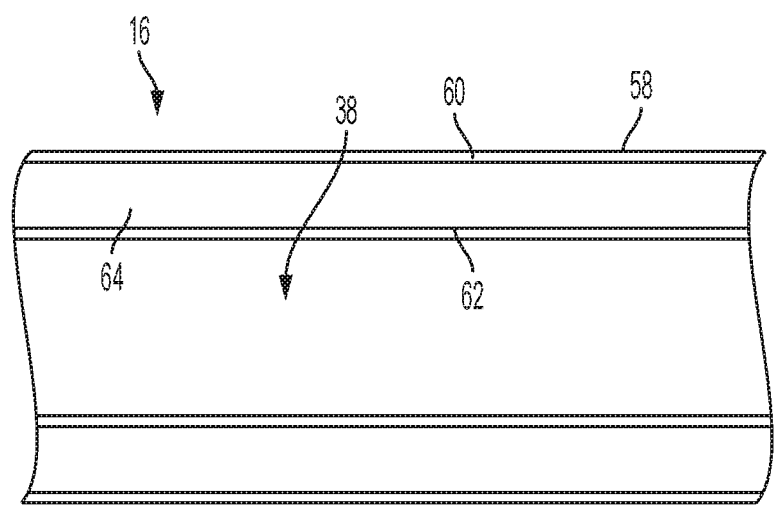
FIG. 6 illustrates a cross-sectional side view of a fifth example of the extruded silicone material.

FIG. 6 illustrated a cross-sectional side view of the hollow element 16 prior to being inflated and fully cured. Extrusion of the hollow element 16 using the spiral mandrel 42 shown in FIG. 5 may result in the wall 58 of the hollow element 16 having three distinct layers including an outer surface, an inner surface, and an interior portion. The outer surface 60 and inner surface 62 of the wall 58 of the hollow element 16 may be created having a laminar flow, wherein the molecular chains of the material are aligned lengthwise in the direction of the flow of the material. Such a configuration may allow the outer surface 60 and inner surface 62 to resist tears or material flaws which occur at an angle offset from the direction of flow of the hollow element 16. However, the outer surface 60 and the inner surface 62 having a laminar flow may permit flaws to develop along the axis of the direction of flow of the hollow element 16.

The interior portion 64 of the wall 58 of the hollow element 16 may be formed having a turbulent flow, wherein the molecular chains of the material are positioned in random or semi-random directions. Turbulent distribution of the material within the interior portion 64 may resist tears or structural flaws in every direction, but may be less resistant to tears or flaws developing along specific axis, as may be the case in the outer surface 60 and outer surface 62 having been formed with a laminar flow. The combination of the laminar outer surface 60, the turbulent interior portion 64, and the laminar inner surface 62 may result in a hollow element that is more resistant to tearing, to puncturing, or to failing due to structural flaws.

Figure 7:
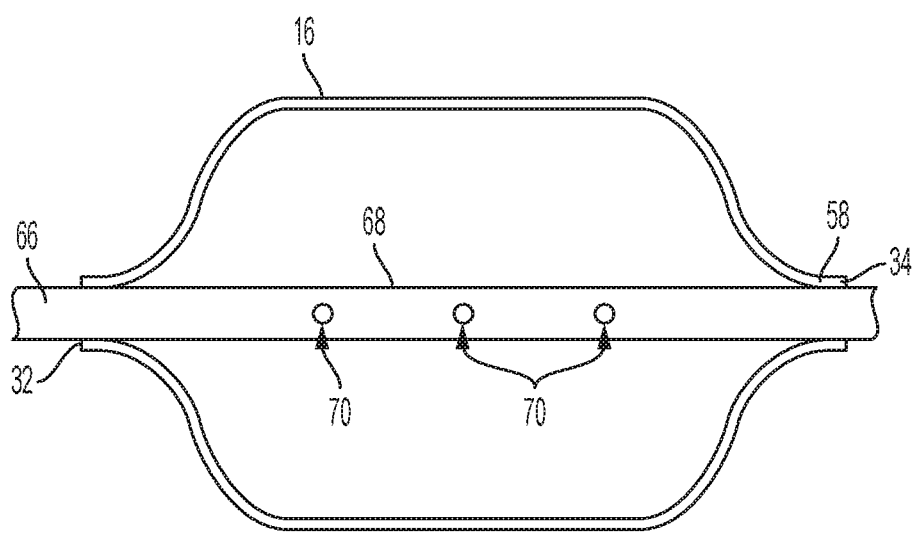
FIG. 7 illustrates a partial cross-sectional side view of a first example of a catheter.

FIG. 7 illustrates a cross-sectional side view of a catheter 66 including the balloon formed from the hollow element 16. After the hollow element 16 has been fully cured into a balloon, the hollow element 16 may be secured to an outer surface 68 of the catheter 66. The hollow element 16 may be secured to the outer surface 68 of the catheter 66 by melting the first end 32 and the second end 34 of the hollow element 16 to mix with the material of the outer surface 68 of the catheter 66. The hollow element 16 may be positioned such that the first end 32 and the second end 34 are arranged between inflation lumens 70 of the catheter 66 to allow for inflation of the hollow element 16.

Once the balloon hollow element 16 has been coupled to the outer surface 68 the catheter 66, the hollow element 16 may be folded against the outer surface 68 of the catheter 66 to allow the catheter 66 to be inserted into a body cavity.

In some embodiments, the lumen 38 of the hollow element 16 may only be open on the first end 32. In such embodiments, the hollow element 16 may be coupled to an end of the catheter 66 by melting only the first end 32 of the hollow element 16 to the outer surface 68 of the catheter 66.

Furthermore, although specific components are described above, methods, systems, and articles of manufacture described herein may include additional, fewer, or different components.

Figure 8:
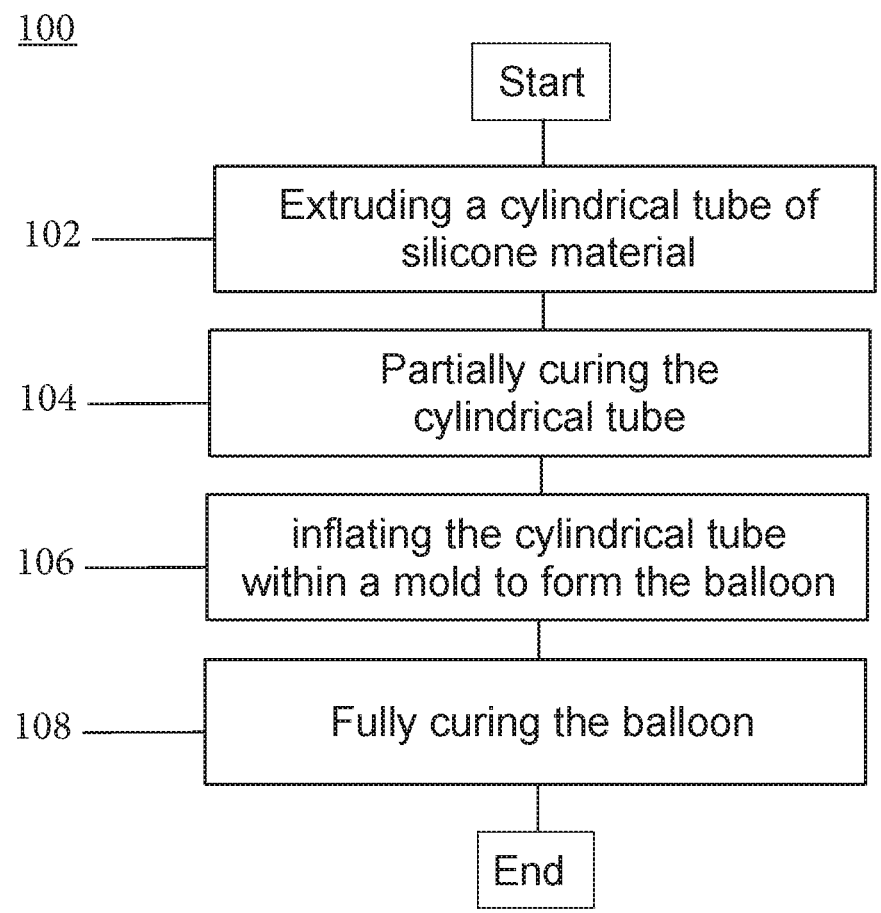
FIG. 8 illustrates a flow diagram of operations to form a balloon for a medical device.

FIG. 8 illustrates a flow diagram of operations (100) to form a balloon from a hollow element 16 for a medical device. The operations may include fewer, additional, or different operations than illustrated in FIG. 8. Alternatively or in addition, the operations may be performed in a different order than illustrated.

Initially, the hollow element 16 is extruded from the extruder 12 (102). The hollow element 16 may, for example, be a cylindrical tube made of liquid silicone rubber material. After extruding the hollow element 16, the hollow element 16 is partially cured by exposing the hollow element 16 to the first ultraviolet light source 14 (104). The partially cured, semi-solid hollow element 16 is then inflated within the mold 36 to form a balloon (106). Before inflation, the partially cured hollow element 16 may be placed in the mold 36 or may be initially extruded into the mold 36. After inflation of the hollow element 16, the hollow element 16 is fully cured by exposing the hollow element 16 to the second ultraviolet light source 14 (108). The fully cured balloon may then be removed from the mold 36 and coupled to the outer surface 68 of the catheter 66.

In addition to the advantages that have been described, it is also possible that there are still other advantages that are not currently recognized but which may become apparent at a later time. While various embodiments have been described, it will be apparent to those of ordinary skill in the art that many more embodiments and implementations are possible. Accordingly, the embodiments described herein are examples, not the only possible embodiments and implementations.

What is claimed is:

1. A method of forming a balloon for a medical device, comprising:
    extruding a cylindrical tube of silicone material;
    partially curing the cylindrical tube by exposing the cylindrical tube to a first ultraviolet light source;
    inflating the cylindrical tube within a mold to form the balloon; and
    fully curing the balloon by exposing the balloon to a second ultraviolet light source.

2. The method of claim 1, further comprising:
    cutting a length of the cylindrical tube; and
    inserting the length of the cylindrical tube into the mold.

3. The method of claim 1, wherein the first ultraviolet light source has a wavelength which is greater than a wavelength of the second ultraviolet light source.

4. The method of claim 3, wherein the wavelength of the second ultraviolet light source is at least 200 nm.

5. The method of claim 3, wherein the wavelength of the first ultraviolet light source is no more than 520 nm.

6. The method of claim 1, further comprising, coupling the balloon to a catheter by melting a first end and a second end of the balloon to an outer surface of a catheter.

7. The method of claim 6, further comprising folding the balloon against the outer surface of the catheter.

8. The method of claim 1, wherein partially curing the cylindrical tube comprises exposing the cylindrical tube to the first ultraviolet light source for no more than 60 seconds.

9. The method of claim 1, wherein fully curing the cylindrical tube comprises exposing the cylindrical tube to the second ultraviolet light source for no more than 300 seconds.

10. A method of forming a balloon for a medical device, comprising
    extruding liquid silicone rubber to form a hollow element;
    partially curing the hollow element to form a semi-solid tube by exposing the liquid silicone rubber to a first ultraviolet light source;
    inflating the semi-solid tube of the hollow element within a mold; and
    fully curing the hollow element to form a balloon by exposing the semi-solid tube of the hollow element to a second ultraviolet light source.

11. The method of claim 10, wherein extruding the liquid silicone rubber comprises extruding an outer surface of the hollow element with a laminar flow and extruding an inner surface of the hollow element with a laminar flow.

12. The method of claim 11, wherein extruding the liquid silicone rubber comprises extruding an interior portion of the hollow element with a turbulent flow.

13. The method of claim 10, wherein the first ultraviolet light source has an intensity which is less than an intensity of the second ultraviolet light source.

14. The method of claim 10, wherein the liquid silicone rubber of the hollow element is exposed to the first ultraviolet light source for a shorter period of time than the semi-solid tube of the hollow element is exposed to the second ultraviolet light source.

* * * * *